（12） United States Patent
Liang et al.

(10) Patent No.: US 11,372,121 B1
(45) Date of Patent: Jun. 28, 2022

(54) METHOD FOR TESTING AND EXTRACTING PALEO-TECTONIC GEOSTRESS BASED ON ROCK CORE

(71) Applicant: SOUTHWEST PETROLEUM UNIVERSITY, Chengdu (CN)

(72) Inventors: Lixi Liang, Chengdu (CN); Xiangjun Liu, Chengdu (CN); Jian Xiong, Chengdu (CN); Yi Ding, Chengdu (CN); Wen Zhang, Chengdu (CN)

(73) Assignee: SOUTHWEST PETROLEUM UNIVERSITY, Chengdu (CN)

( * ) Notice: Subject to any disclaimer, the term of this patent is extended or adjusted under 35 U.S.C. 154(b) by 0 days.

(21) Appl. No.: 17/581,101

(22) Filed: Jan. 21, 2022

(30) Foreign Application Priority Data

Mar. 18, 2021 (CN) .......................... 202110290727.8

(51) Int. Cl.
*G01V 1/00* (2006.01)
*G01N 3/40* (2006.01)

(52) U.S. Cl.
CPC .............. *G01V 1/001* (2013.01); *G01N 3/40* (2013.01); *G01N 2203/0076* (2013.01)

(58) Field of Classification Search
CPC ... G01V 1/001; G01N 3/40; G01N 2203/0076
USPC .......................................................... 73/584
See application file for complete search history.

(56) References Cited

U.S. PATENT DOCUMENTS 4,107,981 A * 8/1978 Kanagawa ............... G01N 3/08
73/806

FOREIGN PATENT DOCUMENTS

| CN | 101162177 A | * | 4/2008 |
|---|---|---|---|
| CN | 101162177 A | | 4/2008 |
| CN | 204630758 U | * | 9/2015 |
| CN | 204630758 U | | 9/2015 |
| CN | 105156103 A | | 12/2015 |
| CN | 107121703 A | | 9/2017 |
| CN | 107505207 A | | 12/2017 |
| CN | 107588877 A | | 1/2018 |
| CN | 111856573 A | | 10/2020 |

(Continued)

OTHER PUBLICATIONS

Zhang Chong-Yang, Xiong Jian, Liang Li-Xi, Liu Xiang-Jun and Zhang Xu; Experimental Study on the Mechanical Properties of the Rocks in the Conglomerate Formation of the KS Area; Science Technology and Engineering, 2020, 20(27): 11038-11044; State Key Laboratory of Oil and Gas Reservoir Geology and Exploitation, Southwest Petroleum University, Chengdu 610500, China.

(Continued)

*Primary Examiner* — Marrit Eyassu

(57) ABSTRACT

A method for testing and extracting paleo-tectonic geostress based on rock core, including: selecting rock cores in different tectonic periods; preparing standard cylindrical samples from the rock cores in a specific orientation; subjecting the samples to an acoustic emission test to test paleo-stresses of multiple tectonic periods and obtain paleo-tectonic stress data sequence; based on a correlation analysis and an Euclidean distance of the stress data sequence, stripping and extracting multi-level Kaiser stress points of the acoustic emission of rock cores from different formations, so as to calculate and evaluate the ground stress of an evaluated formation in an evaluated paleo-tectonic period.

6 Claims, 1 Drawing Sheet

(56) References Cited

FOREIGN PATENT DOCUMENTS

CN 112129448 A 12/2020

OTHER PUBLICATIONS

Wang Lianguo and Lu Yinlong; Ground stress and its impact on the stability of the surrounding rock in the Lüliang mining area; Mining Science and Technology (China) 21 (2011) 625-630; State Key Laboratory of Geomechanics and Deep Underground Engineering, Xuzhou 221008, China.

Zhong Ziqiang, Liu Xiangjun, Liu Shiqiong and Liang Lixi; Logging prediction model of rock mechanical parameters and its applications in conglomerate formation; Science Technology and Engineering, 2018, 18(8): 181-186; State Key Laboratory of Oil and Gas Reservoir Geology and Exploitation, Southwest Petroleum University, Chengdu 610500, China.

Jian Xiong, Kaiyuan Liu, Xiangjun Liu, Lixi Liang and Chongyang Zhang; Influences of bedding characteristics on the acoustic wave propagation characteristics of shales; Petroleum, 2020, vol. 7(1), 33-38; State Key Laboratory of Oil and Gas Reservoir Geology and Exploitation, Southwest Petroleum University, Chengdu, China.

He Jian; The Study of Geostress Characteristics and Engineering Areas Geostress Inversion in the Southwest Region; CNKI, 2017; Chongqing University, Chongqing, China.

Jia Yipeng, Study on Prediction Method and Theorial model of rock burst, CNKI, 2014, Zhejiang University, Zhejiang, China.

* cited by examiner

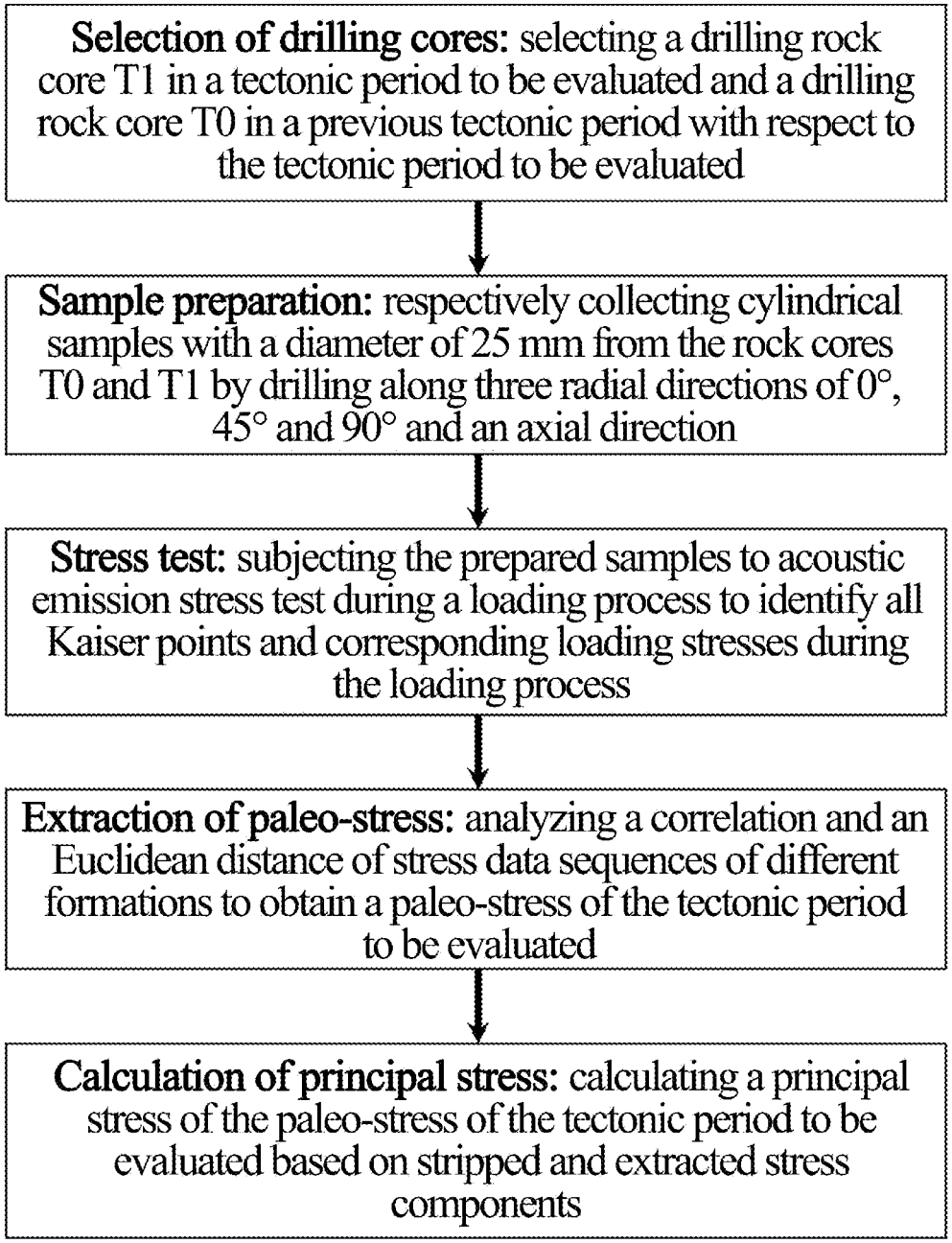

METHOD FOR TESTING AND EXTRACTING PALEO-TECTONIC GEOSTRESS BASED ON ROCK CORE

CROSS-REFERENCE TO RELATED APPLICATIONS

This application claims the benefit of priority from Chinese Patent Application No. 202110290727.8, filed on Mar. 18, 2021. The content of the aforementioned application, including any intervening amendments thereto, is incorporated herein by reference in its entirety.

TECHNICAL FIELD

The application relates to tectonic structure and mechanical measurement, and more particularly to a method for testing and extracting paleo-tectonic geostress based on rock core.

BACKGROUND

Paleo-stress is a critical basic parameter for the paleo structure restoration, structural fracture prediction, and fault activity analysis. Scientific and accurate evaluation of paleo-stress is of great significance for the structural evolution analysis, oil-gas reservoir prediction, mineral resource identification and evaluation, and fault activity prediction. Currently, the exploration about the paleo-stress is mainly performed by inversion based on faults/joints and other structural occurrences and their dynamic characteristics, calcite e-twin analysis, and stress measurement based on rock acoustic emission.

Considering that the rock acoustic emission possesses the characteristics of multiple stages and directivity for stress "memorization", the paleo-stress evaluation method based on rock acoustic emission can be adopted to measure the multi-stage tectonic stress experienced by the rock and level of the ground stress in different directions. However, the rock acoustic emission fails to separate the measured paleo-stresses of multiple periods, and realize the one-to-one correspondence with multiple paleo-tectonic periods and the period division and coordination, thereby making it difficult to extract and analyze the ground stress in a specific tectonic period. Although the existing paleo-tectonic stress qualitative analysis method through the combination of field joints/faults can realize the period division and coordination of paleo-stresses and paleo-structures, it still struggles with complicated operation, strict requirements for the analyst in the tectonic structure professional level, heavy work intensity, and poor reliability.

SUMMARY

In view of the defects in the prior art that the existing multi-stage analysis method fails to enable the period division and coordination of paleo-stresses and paleo-structures, and has large work intensity, and poor reliability, this disclosure provides a method for testing and extracting rock core under paleo-tectonic ground stress to complete the fast and scientific extraction and evaluation of the ground stress in a specific tectonic period.

Technical solutions of the disclosure are described as follows.

The present disclosure provides a method for measuring and extracting paleo-tectonic ground stress based on rock core, comprising:

(S1) selecting a drilling rock core T1 in a tectonic period to be evaluated and a drilling rock core T0 in a previous tectonic period with respect to the tectonic period to be evaluated; and calibrating a radial direction consistency of the drilling rock cores T0 and T1 to ensure that the drilling rock cores T0 and T1 have the same geographic orientation in a radial direction relative to 0°;

(S2) obtaining standard cylindrical samples with a diameter of 25 mm and a length of 50 mm respectively from the drilling rock cores T0 and T1 by drilling; and cutting and grinding both ends of each of the standard cylindrical samples;

(S3) subjecting the standard cylindrical samples obtained in step (S2) to an acoustic emission stress test to identify a Kaiser point of acoustic emission of each of the standard cylindrical samples and a corresponding loading stress during a loading process;

(S4) calculating an average value of a loading stress data sequence corresponding to the Kaiser point of the acoustic emission of each of standard cylindrical samples in the same orientation to obtain a paleo-stress data sequence of a corresponding formation in a corresponding orientation, expressed as follows:

$$DStri\_j = \frac{\sum_{m}^{M} DStri\_{jm}}{M} (M \geq 3); \quad (1)$$

wherein DStr represents a paleo-stress data; i is 0 or 1, and when i is 0, it represents the drilling rock core T0, and when i is 1, it represents the drilling rock core T1; j represents an orientation of the standard cylindrical sample; M represents the number of the standard cylindrical samples in the same orientation, and M≥3; m represents a m-th stress data sequence, and 1≤m≤M;

(S5) setting the number of a stress data of standard cylindrical samples from T0 in a j orientation as N0, and setting the number of a stress data of standard cylindrical samples from T1 in the j orientation as N1; and randomly selecting N1 data from N0 data in a stress data sequence of the standard cylindrical samples from T0, followed by permutation to construct a stress data sequence to be evaluated in the j orientation;

(S6) calculating a correlation coefficient and an Euclidean distance between the stress data sequence to be evaluated constructed in step (S5) and a stress data sequence of the standard cylindrical samples from T1 in the same orientation obtained in step (S4) respectively through equations (2) and (3), and calculating a ratio of the correlation coefficient to the Euclidean distance via equation (4):

$$Rt_{ij} = \frac{\sum_{k}^{N1} (\sigma_{ik} - \overline{\sigma}_i)(\sigma_{jk} - \overline{\sigma}_j)}{\sqrt{\sum_{k}^{N1} (\sigma_{ik} - \overline{\sigma}_i)^2 \cdot \sum_{k}^{n} (\sigma_{jk} - \overline{\sigma}_j)^2}} \quad (2)$$

$$Do_{ij} = \sqrt{\sum_{k}^{N1} (\sigma_{ik} - \sigma_{jk})^2} \quad (3)$$

$$R_{ij} = \frac{Rt_{ij}}{Do_{ij}} \quad (4)$$

wherein $Rt_{ij}$ is a correlation coefficient between a stress data sequence DStri of a formation Ti in a certain orientation and a stress data sequence DStrj of a formation Tj in the same orientation;

$Do_{ij}$ is an Euclidean distance between the stress data sequence DStri of the formation Ti in a certain orientation and the stress data sequence DStrj of the formation Tj in the same orientation;

$R_{ij}$ is a ratio of the correlation coefficient $Rt_{ij}$ to the Euclidean distance $Do_{ij}$;

$\sigma_{ik}$ is a k-th stress value in the stress data sequence DStri of the formation Ti in a certain orientation;

$\sigma_{jk}$ is a k-th stress value in the stress data sequence DStrj of the formation Tj in a certain orientation; and $\overline{\sigma}_i$ is an average value of $\sigma_{ik}$, and $\sigma_{jk}$ is an average value of $\sigma_{jk}$;

(S7) based on calculation results obtained in step (S6), obtaining a maximum correlation coefficient Rt and a minimum Euclidean distance Do between stress data sequences to be evaluated in the same orientation and the stress data sequence of the standard cylindrical samples from T1 in the same orientation obtained in step (S4) respectively through equations (5) and (6), and obtaining a maximum ratio $R_{max}$ of the correlation coefficient to the Euclidean distance through equation (7):

$$Rt = \text{Max}(Rt_{ij-t}) \quad (5)$$

$$Do = \text{Min}(Do_{ij-t}) \quad (6)$$

$$R_{max} = \text{Max}\left(\frac{Rt_{ij-t}}{Do_{ij}-t}\right) \quad (7)$$

wherein $Rt_{ij-t}$ is a correlation coefficient between a t-th stress data sequence to be evaluated constructed in step (S5) and the stress data sequence of the standard cylindrical sample from T1 in the same orientation in step (S4), and $Do_{ij-t}$ is an Euclidean distance between the t-th stress data sequence to be evaluated constructed in step (S5) and the stress data sequence of the standard cylindrical samples from T1 in the same orientation in step (S4);

(S8) taking a stress data sequence to be evaluated corresponding to the maximum correlation coefficient Rt, the minimum Euclidean distance Do, and the maximum ratio $R_{max}$ as a stress data sequence memorized in the formation T0 in the same orientation as the formation T1; wherein a stress data removed from a corresponding stress data sequence of the cylindrical sample from T0 in step (S4) is possessed by the formation T0 but not in the formation T1 in an orientation, and is a paleo-stress data of the formation T0 in the tectonic period to be evaluated; and realizing tripping and an extraction of paleo-stress data in the tectonic period to be evaluated in an analysis orientation; and (S9) calculating a maximum horizontal principal stress, a minimum horizontal principal stress and a vertical principal stress of paleo-tectonic ground stress in the tectonic period to be evaluated by means of equations (8) and (9):

$$\sigma_V = \sigma_V \quad (8)$$
$$\sigma_{H1} = \frac{\sigma_0 + \sigma_{90}}{2} + \frac{\sigma_0 - \sigma_{90}}{2}(1 + \tan^2 2\alpha)$$
$$\sigma_{h2} = \frac{\sigma_0 + \sigma_{90}}{2} - \frac{\sigma_0 - \sigma_{90}}{2}(1 + \tan^2 2\alpha)$$

-continued
$$\tan 2\alpha = \frac{\sigma_0 + \sigma_{90} - 2\sigma_{45}}{\sigma_0 + \sigma_{90}}; \quad (9)$$

wherein $\sigma_{H1}$ is a maximum horizontal principal stress of a formation in the tectonic period to be evaluated; $\sigma_{H2}$ is a minimum horizontal principal stress of the formation in the tectonic period to be evaluated; $\sigma_V$ is the vertical principal stress of the formation in the tectonic period to be evaluated; and $\sigma_0$ is a stress component relative to an 0° orientation, $\sigma_{45}$ is a stress component relative to an 45° orientation, and $\sigma_{90}$ is a stress component relative to an 90° orientation.

In an embodiment, in step (S1), the drilling rock core T1 is collected from a formation in the tectonic period to be evaluated; the drilling rock core T0 is collected from a formation in the previous tectonic period with respect to the tectonic period to be evaluated; and the formation in the tectonic period to be evaluated and the formation in the previous tectonic period both have a gentle structure and a formation dip of no more than 15°; the drilling rock core T1 and the drilling rock core T0 both have a diameter of no less than 65 mm; and the drilling rock core T0 and the drilling rock core T1 are both free of visible fracture and development of a structural plane.

In an embodiment, in step (S2), the standard cylindrical samples are collected from the rock cores T0 and T1 respectively along three radial directions of 0°, 45° and 90° and an axial direction.

In an embodiment, in step (S4), stress data sequences of at least 3 standard cylindrical samples in the same orientation are averaged to eliminate an effect of an uncertain factor on stress test.

In an embodiment, in step (S5), the number of the stress data sequence to be evaluated in the j orientation is N0(N0–1)(N0–2) . . . (N0–N1+1).

In an embodiment, in step (S8), the maximum correlation coefficient Rt and the minimum Euclidean distance Do between N0(N0–1)(N0–2) . . . (N0–N1+1) stress data sequences to be evaluated and the stress data sequence of the standard cylindrical samples from T1 in the same orientation, and the maximum ratio $R_{max}$ of the correlation coefficient to the Euclidean distance are used to determine a stress data sequence memorized formation T0 that is the same as a stress data sequence of the formation T1 at the same orientation.

Compared with the prior art, this application has the following beneficial effects.

The method provided herein for testing and extracting paleo-tectonic geostress based on rock core realizes the fast and scientific extraction and evaluation of the paleo-stress in a specific tectonic period, and can provide effective paleo-stress information for the paleo-stress restoration, paleo-structural restoration, fracture prediction of reservoir structure, fault activity analysis, and structural dynamics analysis. Moreover, the method of the disclosure is also of great significance for the prediction and evaluation of oil-gas reservoir, researches on the paleo-tectonic evolution, mineral exploration and fault activity prediction.

BRIEF DESCRIPTION OF THE DRAWINGS

The FIGURE is a flowchart of test and extraction of paleo-tectonic geostress based on rock core according to an embodiment of this disclosure.

DETAILED DESCRIPTION OF EMBODIMENTS

This application will be described in detail below with reference to embodiments and accompanying drawings to make the objectives, technical solutions, and advantages of this application clearer. Obviously, provided below are merely some embodiments of this application, which are not intended to limit the application. Other embodiments obtained by those of the ordinary skill in the art based on the embodiments provided herein without paying any creative effort shall fall within the scope of the present application.

As shown in the FIGURE, a method for testing and extracting paleo-tectonic geostress based on rock core is provided, which includes the following steps.

1. Selection of Rock Cores

A drilling rock core T1 in a tectonic period to be evaluated and a drilling rock core T0 in a previous tectonic period with respect to the evaluated tectonic period are selected, where the formation in the tectonic period to be evaluated and the formation in the previous tectonic period both have a gentle structure and a formation dip of no more than 15°. The drilling rock core T1 and the drilling rock core T0 both have a diameter of no less than 65 mm. The drilling rock core T0 and the drilling rock core T1 are both free of visible fracture and development of a structural plane. A radial direction consistency of the drilling rock cores T0 and T1 are calibrated to ensure that the drilling rock cores T0 and T1 have the same geographic orientation in a radial direction relative to 0°.

2. Preparation of Samples

Standard cylindrical samples $T0_{-0}$, $T0_{-45}$, $T0_{-90}$ and $T0_{-V}$ with a diameter of 25 mm and a length of 50 mm are obtained respectively from the drilling rock core T0 along three radial directions of 0°, 45° and 90° and an axial direction by drilling. Both ends of each of the standard cylindrical samples are cut and ground. At least 3 samples are obtained in each orientation by drilling, i.e., at least 12 cylindrical samples with a diameter of 25 mm are obtained and prepared from the drilling rock core T0 by drilling. Equally, standard cylindrical samples $T1_{-0}$, $T1_{-45}$, $T1_{-90}$ and $T1_{-V}$ with a diameter of 25 mm and a length of 50 mm are respectively obtained from the drilling rock core T1 along three radial directions of 0°, 45° and 90° and an axial direction by drilling. At least 3 samples are obtained in each orientation by drilling.

3. Acoustic Emission Test

Six groups of the standard cylindrical samples $T0_{-0}$, $T0_{-45}$, $T0_{-90}$, $T0_{-V}$, $T1_{-0}$, $T1_{-45}$, $T1_{-90}$ and $T1_{-V}$ (at least 3 samples in each group) prepared by drilling are subjected to continuous loading along the axial direction and the acoustic emission events during a loading process are recorded continuously in real time synchronously. The result of the acoustic emission is analyzed to identify a Kaiser points of acoustic emission of each of the standard cylindrical samples and a corresponding loading stress during the loading process.

4. Obtaining of Paleo-Stress Data Sequence of Formation

A paleo-stress data sequence is formed by the loading stress corresponding to the Kaiser point of each of the standard cylindrical samples. To eliminate an effect of an uncertain factor in a data, an average value of the paleo-stress data sequence of each standard cylindrical sample in each group (including at least 3 samples) is calculated, which is expressed as follows:

$$DStri_{-j} = \frac{\sum_{m}^{M} DStri_{-jm}}{M} (M \geq 3); \quad (1)$$

after that, paleo-stress data sequences of corresponding formations along corresponding orientations are obtained, that is, the stress data sequences $DStr0_{-0}$, $DStr0_{-45}$, $DStr0_{-90}$, $DStr0_{-V}$ and $DStr1_{-0}$, $DStr1_{-45}$, $DStr1_{-90}$, $DStr1_{-V}$ of $T0_{-0}$, $T0_{-45}$, $T0_{-90}$, $T0_{-V}$, $T1_{-0}$, $T1_{-45}$, $T1_{-90}$ and $T1_{-V}$ are respectively obtained, which is shown as follow:

$DStr0_{-0} = \{Str0_{-0-1}, Str0_{-0-2} \ldots Str0_{-0-i} \ldots Str0_{-0-N0}\}$ $DStr0_{-45} = \{Str0_{-0-1}, Str0_{-45-2} \ldots Str0_{-45-i} \ldots Str0_{-45-N0}\}$ $DStr0_{-90} = \{Str0_{-0-1}, Str0_{-90-2} \ldots Str0_{-90-i} \ldots Str0_{-90-N0}\}$ $DStr0_{-v} = \{Str0_{-0-1}, Str0_{-v-2} \ldots Str0_{-v-i} \ldots Str0_{-v-N0}\}$ $DStr1_{-0} = \{Str1_{-0-1}, Str1_{-0-2} \ldots Str1_{-0-i} \ldots Str1_{-0-N0}\}$ $DStr1_{-45} = \{Str1_{-0-1}, Str1_{-45-2} \ldots Str1_{-45-i} \ldots Str1_{-45-N0}\}$ $DStr1_{-90} = \{Str1_{-0-1}, Str1_{-90-2} \ldots Str1_{-90-i} \ldots Str1_{-90-N0}\}$ $DStr1_{-v} = \{Str1_{-0-1}, Str1_{-v-2} \ldots Str1_{-v-i} \ldots Str1_{-v-N0}\}$

TABLE 1

Stress data sequences of Kaiser points of rock cores in different orientations of each formation

| Formation | Data sequence | Sampling direction | Level 1 | Level 2 | Level 3 | Level 4 |
|---|---|---|---|---|---|---|
| T1 | $DStr1_{-0}$ | 0 | 31.686 | 54.015 | 63.888 | — |
|  | $DStr1_{-45}$ | 45 | 13.982 | 38.142 | 44.147 | — |
|  | $DStr1_{-90}$ | 90 | 20.639 | 40.862 | 47.341 | — |
|  | $DStr1_{-v}$ | v | 21.837 | 44.691 | 52.179 | — |
| T0 | $DStr0_{-0}$ | 0 | 33.423 | 53.056 | 58.188 | 65.383 |
|  | $DStr0_{-45}$ | 45 | 14.017 | 36.117 | 41.047 | 46.999 |
|  | $DStr0_{-90}$ | 90 | 21.143 | 40.994 | 47.219 | 63.873 |
|  | $DStr0_{-v}$ | v | 23.007 | 43.424 | 52.377 | 64.779 |

5. Stripping and Analysis of Paleo-Stress Data 5.1 Stripping and Analysis of Paleo-Stress Data in 0° Orientation (1) The number N0 of the stress data in the stress data sequence in the orientations of a formation $DStr0_{-0}$, and the number N1 of the stress data in the stress data sequence in the orientations of a formation $DStr1_{-0}$ are obtained. NN=N0−N1 data are randomly removed from a stress data sequence $DStr0_{-0}$ to construct a stress data sequence $DStr0l$ with the same amount of stress as that of a stress data sequence $DStr1_{-0}$, i.e., N1 data are extracted from the stress data sequence $DStr0_{-0}$ and then subjected to a permutation to construct a stress data sequence, which is expressed as follows:

$DStr01_{-0} = \{Str1_{-0-1}, Str1_{-0-2} \ldots Str1_{-0-i} \ldots Str0_{-0-N1}\};$ N0(N0−1)(N0−2) . . . (N0−N1+1) stress data sequences $DStr0l$ with N1 stress data are constructed in total.

As shown in Table 1, there are 3 stress data in a stress data sequence of the formation T1, i.e., N1=3; there are 4 stress data in a stress data sequence of the formation T0, i.e., N0=4. The 3 data are extracted from the stress data sequence $DStr0_{-0}$ to form 12 data sequences $DStr0l$ in total, the results of which are shown in Table 2.

TABLE 2

Stress data sequences DStr01 to be evaluated extracted and
constructed from stress data sequences of formation T0

| Stress data sequence | Sequence | Level 1 | Level 2 | Level 3 | Level 4 | Notes |
|---|---|---|---|---|---|---|
| DStr1$_{-0}$ |  | 31.686 | 54.015 | 63.888 | — |  |
| DStr0$_{-0}$ |  | 33.423 | 53.056 | 58.188 | 65.383 |  |
| DStr01 | 1 | 33.423 | 53.056 | 58.188 |  | Extracted |
| DStr01 | 2 | 33.423 | 58.188 | 65.383 |  | data |
| DStr01 | 3 | 33.423 | 53.056 | 65.383 |  | sequences |
| DStr01 | 4 | 53.056 | 58.188 | 65.383 |  | to be |
| DStr01 | 5 | 53.056 | 58.188 | 33.423 |  | evaluated |
| DStr01 | 6 | 53.056 | 65.383 | 33.423 |  |  |
| DStr01 | 7 | 58.188 | 65.383 | 33.423 |  |  |
| DStr01 | 8 | 58.188 | 65.383 | 53.056 |  |  |
| DStr01 | 9 | 58.188 | 33.423 | 53.056 |  |  |
| DStr01 | 10 | 65.383 | 33.423 | 53.056 |  |  |
| DStr01 | 11 | 65.383 | 33.423 | 58.188 |  |  |
| DStr01 | 12 | 65.383 | 53.056 | 58.188 |  |  |

(2) A correlation coefficient and an Euclidean distance between the stress data sequences DStr01 to be evaluated and the stress data sequence DStr1$_{-0}$ are calculated respectively through equations (2) and (3), and a ratio of the correlation coefficient to the Euclidean distance is calculated via equation (4):

where $Rt_{ij}$ is a correlation coefficient between a stress data sequence DStri of a formation Ti in a certain orientation and a stress data sequence DStrj of a formation Tj in the same orientation; $Do_{ij}$ is an Euclidean distance between the stress data sequence DStri of the formation Ti in a certain orientation and the stress data sequence DStrj of the formation Tj in the same orientation; is a ratio of the correlation coefficient $Rt_{ij}$ to the Euclidean distance $Do_{ij}$; $\sigma_{ik}$ is a k-th stress value in the stress data sequence DStri of the formation T1 in a certain orientation, and the corresponding values can be Stri$_{|0-k}$, Stri$_{-45-k}$, Stri$_{-90-k}$, Stri$_{-v-k}$; $\sigma_{ik}$ is a k-th stress value in the stress data sequence DStrj of the formation Tj in a certain orientation, and the corresponding values can be Strj$_{-0-k}$, Strj$_{-45-k}$, Strj$_{-90-k}$, Strj$_{-v-k}$; and $\overline{\sigma}_1$ is an average value of $\sigma_{ik}$, and $\sigma_{jk}$ is an average value of $\sigma_{jk}$.

The correlation coefficient, the Euclidean distance between each stress data sequence DStr01 to be evaluated and the stress data sequence DStr1$_{-0}$ shown in Table 2, and a ratio of the correlation coefficient to the Euclidean distance are calculated, and the results are shown in Table 3.

TABLE 3

Construction of stress data sequence of formation T0 and its correlation
analysis with paleo-stress data sequence in 0° orientation of formation T1

| Stress data sequence | Sequence | Level 1 | Level 2 | Level 3 | Level 4 | Correlation coefficient $Rt_{ij}$ | Euclidean distance $Do_{ij}$ | Ratio of the correlation coefficient to the Euclidean distance RD |
|---|---|---|---|---|---|---|---|---|
| DStr1$_{-0}$ |  | 31.686 | 54.015 | 63.888 | — | — | — | — |
| DStr0$_{-0}$ |  | 33.423 | 53.056 | 58.188 | 65.383 | — | — | — |
| DStr01 | 1 | 33.423 | 53.056 | 58.188 | — | 0.994 | 6.035 | 0.165 |
| DStr01 | 2 | 33.423 | 58.188 | 65.383 | — | 0.996 | 4.761 | 0.209 |
| DStr01 | 3 | 33.423 | 53.056 | 65.383 | — | 0.996 | 2.484 | 0.401 |
| DStr01 | 4 | 53.056 | 58.188 | 65.383 | — | 0.950 | 21.825 | 0.044 |
| DStr01 | 5 | 53.056 | 58.188 | 33.423 | — | −0.589 | 37.446 | −0.016 |
| DStr01 | 6 | 53.056 | 65.383 | 33.423 | — | −0.422 | 38.910 | −0.011 |
| DStr01 | 7 | 58.188 | 65.383 | 33.423 | — | −0.574 | 41.949 | −0.014 |
| DStr01 | 8 | 58.188 | 65.383 | 53.056 | — | −0.206 | 30.805 | −0.007 |
| DStr01 | 9 | 58.188 | 33.423 | 53.056 | — | −0.405 | 35.266 | −0.011 |
| DStr01 | 10 | 65.383 | 33.423 | 53.056 | — | −0.575 | 40.949 | −0.014 |
| DStr01 | 11 | 65.383 | 33.423 | 58.188 | — | −0.422 | 39.900 | −0.011 |
| DStr01 | 12 | 65.383 | 53.056 | 58.188 | — | −0.744 | 34.189 | −0.022 |

$$Rt_{ij} = \frac{\sum\limits_{k}^{N1}(\sigma_{ik} - \overline{\sigma}_i)(\sigma_{jk} - \overline{\sigma}_j)}{\sqrt{\sum\limits_{k}^{N1}(\sigma_{ik} - \overline{\sigma}_i)^2 \cdot \sum\limits_{k}^{n}(\sigma_{jk} - \overline{\sigma}_j)^2}} \quad (2)$$

$$Do_{ij} = \sqrt{\sum\limits_{k}^{N1}(\sigma_{ik} - \sigma_{jk})^2} \quad (3)$$

$$R_{ij} = \frac{Rt_{ij}}{Do_{ij}}; \quad (4)$$

(3) Based on the correlation coefficient and the Euclidean distance between the two data sequences, the same stress data sequence is identified. A maximum correlation coefficient Rt, and a minimum Euclidean distance Do between the stress data sequences to be evaluated and the stress data sequence DStr1$_{-0}$, are obtained respectively through equations (5) and (6), and a maximum ratio $R_{max}$ of the correlation coefficient to the Euclidean distance is obtained through equation (7):

$$Rt = \text{Max}(Rt_{ij-t}) \quad (5)$$

$$Do = \text{Min}(Do_{ij-t}) \quad (6)$$

$$R_{max} = \text{Max}\left(\frac{Rt_{ij-t}}{Do_{ij-t}}\right); \quad (7)$$

where $Rt_{ij-t}$ is a correlation coefficient between a t-th stress data sequence DStr01 to be evaluated and the stress data sequence $DStr1_{-0}$, and $Do_{ij-t}$ is an Euclidean distance between the t-th stress data sequence DStr01 to be evaluated and the stress data sequence $DStr1_{-0}$.

A stress data sequence to be evaluated corresponding to the maximum correlation coefficient Rt, the minimum Euclidean distance Do, and the maximum ratio of the correlation coefficient to the Euclidean distance $R_{max}$ is taken as a stress data sequence memorized in the formation T0 in the same orientation as the formation $T1_{-0}$, where a stress data removed from a corresponding stress data sequence $DStr0_{-0}$ is possessed by the formation T0 but not in the formation T1 in an orientation, and is a paleo-stress data of the formation T0 in the tectonic period to be evaluated. The paleo-stress data in the tectonic period to be evaluated in an analytical orientation is stripped and extracted through the above steps.

5.2 Stripping and Analysis of Paleo-Stress Data in 45° Orientation, 90° Orientation and Axial Direction According to the steps in 5.1, the stress data in the 45° orientation, the 90° orientation and the axial direction orientation in the tectonic period to be evaluated are stripped and extracted.

Table 4 shows a stress data stripped from the stress data sequence of the formation T0 shown in Table 1 the same as the formation T1 and the stress data in the tectonic period to be evaluated

TABLE 4

Stress data sequence of formation T1 included in stress data sequences of formation T0 in all orientations and stress in tectonic period to be evaluated

| Orientation | Stress data sequence | Level 1 | Level 2 | Level 3 | Correlation coefficient $Rt_{ij}$ | Euclidean distance $Do_{ij}$ | Ratio RD of correlation coefficient to Euclidean distance | Stress of evaluated tectonic period |
|---|---|---|---|---|---|---|---|---|
| 0 | $DStr1_{-0}$ | 33.423 | 53.056 | 65.383 | 0.996 | 2.484 | 0.401 | 58.188 |
| 45 | $DStr1_{-45}$ | 14.017 | 36.117 | 46.999 | 0.990 | 3.498 | 0.283 | 41.047 |
| 90 | $DStr1_{-90}$ | 21.143 | 40.994 | 47.219 | 1.000 | 0.535 | 1.869 | 63.873 |
| v | $DStr1_{-v}$ | 23.007 | 43.424 | 52.377 | 0.998 | 1.736 | 0.575 | 64.779 |

6. Calculation of Principal Stress

Based on each stripped and extracted stress component, a maximum horizontal principal stress, a minimum horizontal principal stress and a vertical principal stress of paleo-tectonic ground stress in the tectonic period to be evaluated are calculated by means of equations (8) and (9):

$$\sigma_V = \sigma_V \quad (8)$$
$$\sigma_{H1} = \frac{\sigma_0 + \sigma_{90}}{2} + \frac{\sigma_0 - \sigma_{90}}{2}(1 + \tan^2 2\alpha)$$
$$\sigma_{h2} = \frac{\sigma_0 + \sigma_{90}}{2} - \frac{\sigma_0 - \sigma_{90}}{2}(1 + \tan^2 2\alpha)$$

$$\tan 2\alpha = \frac{\sigma_0 + \sigma_{90} - 2\sigma_{45}}{\sigma_0 + \sigma_{90}}; \quad (9)$$

where $\sigma_{H1}$ is a maximum horizontal principal stress of a formation in the tectonic period to be evaluated; $\sigma_{H2}$ is a minimum horizontal principal stress of the formation in the tectonic period to be evaluated; $\sigma_V$ is the vertical principal stress of the formation in the tectonic period to be evaluated; and $\sigma_0$ is a stress component relative to an 0° orientation, $\sigma_{45}$ is a stress component relative to an 45° orientation, and $\sigma_{90}$ is a stress component relative to an 90° orientation.

Table 5 shows the results of principal stress calculated based on the principal stress components in the tectonic period to be evaluated stripped and extracted in Table 4.

TABLE 5

Calculation results of principal stress

| Stress component (MPa) | | | | Principal stress (MPa) | | |
|---|---|---|---|---|---|---|
| 0° orientation | 45° orientation | 90° orientation | Axial direction | Minimum horizontal stress | Maximum horizontal stress | Vertical stress |
| 58.188 | 41.047 | 63.873 | 64.779 | 58.188 | 63.873 | 64.779 |

The above-mentioned embodiments are merely illustrative of the disclosure, and are not intended to limit the disclosure. It should be understood that any changes, modifications, replacements, and transformations made by those skilled in the art without departing from the spirit and scope of this disclosure shall fall within the scope of the disclosure defined by the appended claims.

What is claimed is:

1. A method for measuring and extracting paleo-tectonic geostress based on rock core, comprising:
   (S1) selecting a drilling rock core T1 in a tectonic period to be evaluated and a drilling rock core T0 in a previous tectonic period with respect to the tectonic period to be evaluated; and calibrating a radial direction consistency of the drilling rock cores T0 and T1 to ensure that the drilling rock cores T0 and T1 have the same geographic orientation in a radial direction relative to 0°;
   (S2) obtaining standard cylindrical samples with a diameter of 25 mm and a length of 50 mm respectively from the drilling rock cores T0 and T1 by drilling; and cutting and grinding both ends of each of the standard cylindrical samples;
   (S3) subjecting the standard cylindrical samples obtained in step (S2) to an acoustic emission stress test to identify a Kaiser point of acoustic emission of each of the standard cylindrical samples and a corresponding loading stress during a loading process;
   (S4) calculating an average value of a loading stress data sequence corresponding to the Kaiser point of the acoustic emission of each of standard cylindrical samples in the same orientation to obtain a paleo-stress data sequence of a corresponding formation in a corresponding orientation, expressed as follows:

$$DStri_{-j} = \frac{\sum_{m}^{M} DStri_{-jm}}{M} (M \geq 3); \quad (1)$$

wherein DStr represents a paleo-stress data; i is 0 or 1, and when i is 0, it represents the drilling rock core T0, and when i is 1, it represents the drilling rock core T1; j represents an orientation of the standard cylindrical sample; M represents the number of the standard cylindrical samples in the same orientation, and M≥3; m represents a m-th stress data sequence, and 1≤m≤M;

(S5) setting the number of a stress data of standard cylindrical samples from T0 in a j orientation as N0, and setting the number of a stress data of standard cylindrical samples from T1 in the j orientation as N1; and randomly selecting N1 data from N0 data in a stress data sequence of the standard cylindrical samples from T0, followed by permutation to construct a stress data sequence to be evaluated in the j orientation;

(S6) calculating a correlation coefficient and an Euclidean distance between the stress data sequence to be evaluated constructed in step (S5) and a stress data sequence of the standard cylindrical samples from T1 in the same orientation obtained in step (S4) respectively through equations (2) and (3), and calculating a ratio of the correlation coefficient to the Euclidean distance via equation (4):

$$Rt_{ij} = \frac{\sum_{k}^{N1} (\sigma_{ik} - \overline{\sigma}_i)(\sigma_{jk} - \overline{\sigma}_j)}{\sqrt{\sum_{k}^{N1} (\sigma_{ik} - \overline{\sigma}_i)^2 \cdot \sum_{k}^{n} (\sigma_{jk} - \overline{\sigma}_j)^2}}; \quad (2)$$

$$Do_{ij} = \sqrt{\sum_{k}^{N1} (\sigma_{ik} - \sigma_{jk})^2}; \quad (3)$$

$$R_{ij} = \frac{Rt_{ij}}{Do_{ij}}; \quad (4)$$

wherein $Rt_{ij}$ is a correlation coefficient between a stress data sequence DStri of a formation Ti in a certain orientation and a stress data sequence DStrj of a formation Tj in the same orientation;

$Do_{ij}$ is an Euclidean distance between the stress data sequence DStri of the formation Ti in a certain orientation and the stress data sequence DStrj of the formation Tj in the same orientation;

$R_{ij}$ is a ratio of the correlation coefficient $Rt_{ij}$ to the Euclidean distance $Do_{ij}$;

$\sigma_{ik}$ is a k-th stress value in the stress data sequence DStri of the formation Ti in a certain orientation;

$\sigma_{jk}$ is a k-th stress value in the stress data sequence DStrj of the formation Tj in a certain orientation; and $\overline{\sigma}_i$ is an average value of $\sigma_{ik}$, and $\overline{\sigma}_{jk}$ is an average value of $\sigma_{ik}$;

(S7) based on calculation results obtained in step (S6), obtaining a maximum correlation coefficient Rt and a minimum Euclidean distance Do between stress data sequences to be evaluated in the same orientation and the stress data sequence of the standard cylindrical samples from T1 in the same orientation obtained in step (S4) respectively through equations (5) and (6), and obtaining a maximum ratio $R_{max}$ of the correlation coefficient to the Euclidean distance through equation (7):

$$Rt = \text{Max}(Rt_{ij-t}) \quad (5)$$

$$Do = \text{Min}(Do_{ij-t}) \quad (6)$$

$$R_{max} = \text{Max}\left(\frac{Rt_{ij-t}}{Do_{ij} - t}\right); \quad (7)$$

wherein $Rt_{ij-t}$ is a correlation coefficient between a t-th stress data sequence to be evaluated constructed in step (S5) and the stress data sequence of the standard cylindrical samples from T1 in the same orientation in step (S4), and $Do_{ij-t}$ is an Euclidean distance between the t-th stress data sequence to be evaluated constructed in step (S5) and the stress data sequence of the standard cylindrical samples from T1 in the same orientation in step (S4);

(S8) taking a stress data sequence to be evaluated corresponding to the maximum correlation coefficient Rt, the minimum Euclidean distance Do, and the maximum ratio $R_{max}$ as a stress data sequence memorized in the formation T0 in the same orientation as the formation T1; wherein a stress data removed from a corresponding stress data sequence of the standard cylindrical samples from T0 in step (S4) is possessed by the formation T0 but not in the formation T1 in an orientation, and is a paleo-stress data of the formation T0 in the tectonic period to be evaluated; and realizing stripping and extraction of paleo-stress data in the tectonic period to be evaluated in an analysis orientation; and (S9) calculating a maximum horizontal principal stress, a minimum horizontal principal stress and a vertical principal stress of paleo-tectonic ground stress in the tectonic period to be evaluated by means of equations (8) and (9):

$$\sigma_V = \sigma_V \quad (8)$$
$$\sigma_{H1} = \frac{\sigma_0 + \sigma_{90}}{2} + \frac{\sigma_0 - \sigma_{90}}{2}(1 + \tan^2 2\alpha)$$
$$\sigma_{h2} = \frac{\sigma_0 + \sigma_{90}}{2} - \frac{\sigma_0 - \sigma_{90}}{2}(1 + \tan^2 2\alpha)$$

$$\tan 2\alpha = \frac{\sigma_0 + \sigma_{90} - 2\sigma_{45}}{\sigma_0 + \sigma_{90}}; \quad (9)$$

wherein $\sigma_{H1}$ is a maximum horizontal principal stress of a formation in the tectonic period to be evaluated; $\sigma_{H2}$ is a minimum horizontal principal stress of the formation in the tectonic period to be evaluated; $\sigma_V$ is the vertical principal stress of the formation in the tectonic period to be evaluated; and $\sigma_0$ is a stress component relative to a 0° orientation, $\sigma_{45}$ is a stress component relative to a 45° orientation, and $\sigma_{90}$ is a stress component relative to a 90° orientation.

2. The method of claim 1, wherein in step (S1), the drilling rock core T1 is collected from a formation in the tectonic period to be evaluated; the drilling rock core T0 is collected from a formation in the previous tectonic period with respect to the tectonic period to be evaluated; and the formation in the tectonic period to be evaluated and the formation in the previous tectonic period both have a gentle structure and a formation dip of no more than 15°; the drilling rock core T1 and the drilling rock core T0 both have a diameter of no less than 65 mm; and the drilling rock core T0 and the drilling rock core T1 are both free of visible fracture and development of a structural plane.

3. The method of claim 1, wherein in step (S2), the standard cylindrical samples are collected from the rock cores T0 and T1 respectively along three radial directions of 0°, 45° and 90° and an axial direction.

4. The method of claim 1, wherein in step (S4), stress data sequences of at least 3 standard cylindrical samples in the same orientation are averaged to eliminate an effect of an uncertain factor on stress test.

5. The method of claim 1, wherein in step (S5), the number of the stress data sequence to be evaluated in the j orientation is N0(N0−1)(N0−2) . . . (N0−N1+1).

6. The method of claim 1, wherein in step (S8), the maximum correlation coefficient Rt and the minimum Euclidean distance Do between N0(N0−1)(N0−2) . . . (N0−N1+1) stress data sequences to be evaluated and the stress data sequence of the standard cylindrical samples from T1 in the same orientation, and the maximum ratio $R_{max}$ of the correlation coefficient to the Euclidean distance are used to determine a stress data sequence memorized formation T0 that is the same as a stress data sequence of the formation T1 at the same orientation.

\* \* \* \* \*